US00PP18452P3

(12) United States Plant Patent
Layt

(10) Patent No.: US PP18,452 P3
(45) Date of Patent: Jan. 22, 2008

(54) ***DIANELLA CAERULEA* PLANT NAMED 'DCMP01'**

(50) Latin Name: *Dianella caerulea*
Varietal Denomination: DCMP01

(75) Inventor: Todd Anthony Layt, New South Wales (AU)

(73) Assignee: Versascapes L.L.C., Mt. Pleasant, SC (US)

( * ) Notice: Subject to any disclaimer, the term of this patent is extended or adjusted under 35 U.S.C. 154(b) by 0 days.

(21) Appl. No.: 11/239,578

(22) Filed: Sep. 29, 2005

(65) Prior Publication Data

US 2006/0075533 P1 Apr. 6, 2006

Related U.S. Application Data

(60) Provisional application No. 60/614,658, filed on Sep. 30, 2004.

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP13,705 P3 * 4/2003 South ..... Plt./263
2006/0075533 P1 * 4/2006 Layt ..... Plt./263

OTHER PUBLICATIONS

Royal Horticultural Society Dictionary of Gardening, 1992, vol. II D–K, McMillan Press, London; Stockton Press, New York, p. 49–50.*
Printout—organicmatters.com.au/dianella–caerula, Mar. 29, 2007.*
Royal Horticultural Society Dictionary of Gardening, 1992, vol. II D–K, McMillan Press, London; Stockton Press, New York, p. 49–50.*
Layt; "Dianella caerulea blue flax lily 'DCMP01,'" *Plant Varieties Journal* 16 (4):124 (Feb. 6, 2004).
Layt; "Dianella caerulea blue flax lily 'DCMP01,'" *Plant Varieties Journal* 17 (1): 591–593 (Apr. 28, 2004).
Austalian Government, IP Australia, Plant Breeder's Rights; database entry for Australian Plant Breeders Right Application No. 2003/292; Variety 'DCMP01' http://pbr.ipaustralia.optus.com.au/docs/2003292. doc.

* cited by examiner

*Primary Examiner*—Anne Marie Grunberg
*Assistant Examiner*—Georgia Helmer
(74) *Attorney, Agent, or Firm*—Myers Bigel Sibley & Sajovec, P.A.

(57) ABSTRACT

'DCMP01' is a distinctive variety of *Dianella caerulea* which is characterized by the combination of its dense growth, slightly spreading and compact growth habit, purple-blue flower color, and short canes with very short internodes, which is unusual for a *Dianella caerulea,* particularly when compared to the 'Sydney Ecotype'. In addition, 'DCMP01' is less prone to falling over than the parent type.

2 Drawing Sheets

Latin name of the genus and species: The Latin name of the novel variety disclosed herein is *Dianella caerulea.*

Variety denomination: The inventive variety of *Dianella caerulea* disclosed herein has been given the varietal denomination 'DCMP01'.

BACKGROUND OF THE INVENTION

The present invention relates to a new and distinct perennial Blue Flax Lilly variety of *Dianella caerulea,* which has been given the varietal denomination of 'DCMP01'. Its market class is that of an ornamental grass-like plant. 'DCMP01' is intended for use in landscaping and as a decorative grass-like plant.

An application for plant breeders' rights for variety 'DCMP01' has been filed with the Australian Plant Breeders' Rights Office, and was first gazetted in the Plant Varieties Journal in October 2003 under Application No. 2003/292.

Parentage. The *Dianella caerulea* variety 'DCMP01' was first discovered in October 1996 in an Australian nursery in Clarendon, New South Wales, after an extensive breeding program. The 'DCMP01' parent, 'Sydney Ecotype'

(unpatented), is characterized by a tall plant height, medium plant density, medium length aerial stems and yellow-green leaf colour.

In 1995, *Dianella* species were grown together in an open bed covering approximately 250 square meters of area. They were grown in groups of species and ecotypes including *Dianella caerulea* collected from the Sydney area, and other regions. The other *Dianella* species present were *longifolia, revoluta* and *tasmanica.* The plants were open pollinated with possible assisted pollination from general shaking of flower stems onto each other.

Seeds were collected and sown from the 'Sydney Ecotype' plants in December 1995. Approximately 30,000 plants were grown. In October 1996, using the selection criteria of compact growth habit and very short aerial stems (canes) with very short internodes, a single plant was identified as having these characteristics. This plant was selected, potted into a 140 mm pot for further evaluation and named 'DCMP01'.

Asexual reproduction. 'DCMP01' was first asexually propagated by division in April 1997, in the state of New South Wales, Australia. It was asexually reproduced again during November 1997 and April 1998 and confirmed to be stable in character. The distinctive characteristics of the inventive variety, 'DCMP01', have remained stable and true to type from generation to generation through successive cycles of asexual reproduction including vegetative division and micropropagation.

SUMMARY OF THE INVENTION

'DCMP01' is a distinctive variety of *Dianella caerulea* which is characterized by the combination of its dense growth, slightly spreading and compact growth habit, purple-blue flower colour, and short canes with very short internodes, which is unusual for a *Dianella caerulea,* particularly when compared to the 'Sydney Ecotype'. In addition, 'DCMP01' is less prone to falling over than the parent type.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella caerulea.*

BOTANICAL DESCRIPTION OF THE PLANT

The following is a detailed botanical description of a new and distinct variety of a *Dianella caerulea* ornamental grass-like plant known as 'DCMP01'. The descriptions disclosed herein are based upon observations of the plant grown in 140 mm nursery pots and field plots in New South Wales, Australia. The plants were approximately 12-months-old at the time of observation. All colors cited herein refer to The Royal Horticultural Society Colour Chart (The Royal Horticultural Society, London, 2001 edition).

Those skilled in the art will appreciate that certain characteristics will vary with older or, conversely, younger plants. 'DCMP01' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
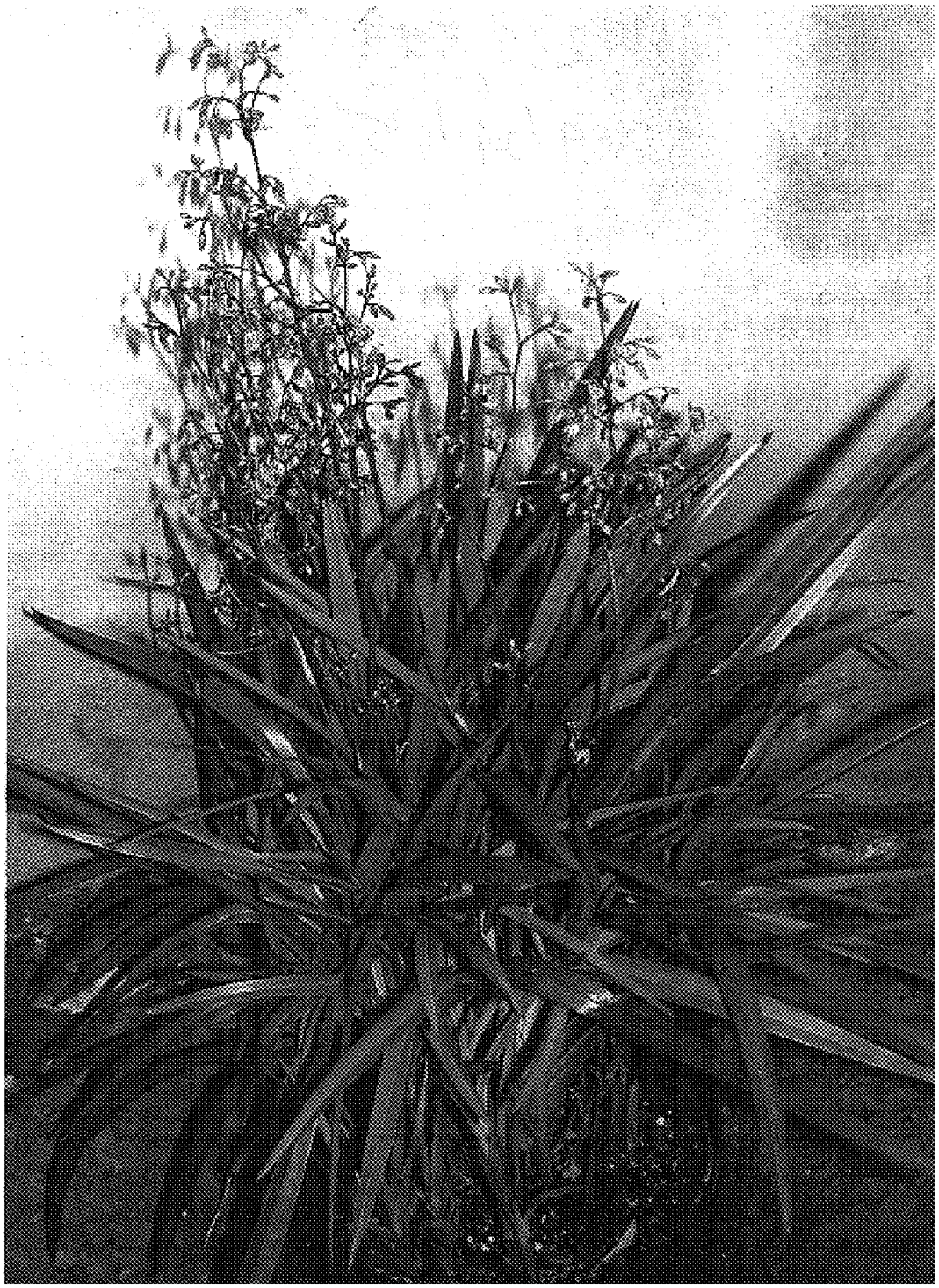
FIG. 1 shows a 'DCMP01' plant and illustrates the unusually short internodes located on short canes and a medium height flower spike that is characteristic of the variety.
Figure 2:
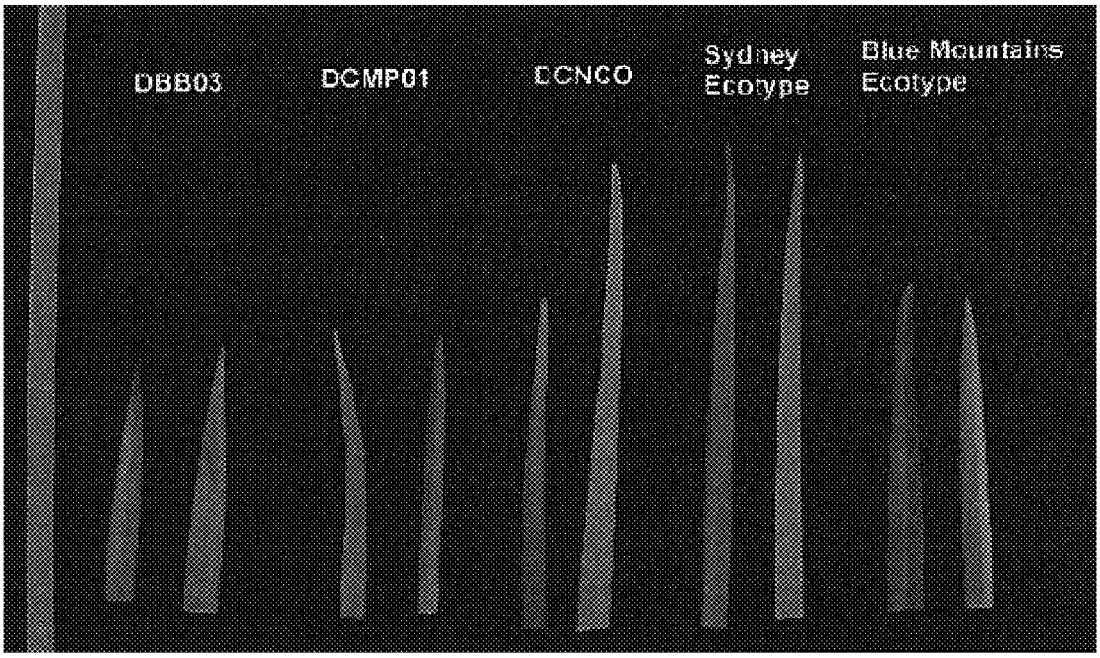
FIG. 2 shows the variation in leaf width and glaucosity among the five *Dianella caerulea* varieties included in the comparison study.

'DCMP01' is a perennial *Dianella caerulea* plant, which was produced through an innovative breeding program. After its selection, 'DCMP01' was asexually propagated by division and micropropagation. 'DCMP01' has dense growth, slightly spreading and compact growth habit, short rhizome form, purple-blue flower colour, unusually short internodes located on short canes, and a reduced tendency to fall over at maturity. A botanical description of 'DCMP01' and a comparison with other varieties of *Dianella caerulea* are provided below. A representative *Dianella caerulea* 'DCMP01' plant is shown in FIG. 1.

Technical Description of the Variety

Growth habit: 'DCMP01' is a short, rhizomatous plant forming a semi-compact tussock. Its growth habit is erect, the height is short (mean 24.6 cm), and the density of shoots is strong.

Stem: Length of internodes is short (less than 10 mm). The Sydney ecotype has internode length which is long (greater than 20 mmm) creating long aerial stem length (also known as canes).

Foliage: Leaf attitude erect, width medium (mean 12.2 mm), upper side colour with waxiness removed yellow-green (RHS 147A), lower side colour with waxiness removed yellow-green (RHS 147B), upper side glaucosity weak, shape ligulate, apex acute, cross section concave, cross-sectional shape with midrib keeled, spines on margin absent, spines on lower side midrib absent.

Basal sheath: Anthocyanin colour red-brown (RHS 178A-B fading to 182B), intensity of anthocyanin colour weak.

Inflorescence: The inflorescence (flower spike) is purple-blue (approximately RHS 83C) with a longer than average length (range 50-60 cm) when compared to *Dianella caerulea* 'DCNCO' (U.S. Plant patent application Ser. No. 11/239,579 filed Sep. 29, 2005; Australian Plant Breeders Rights Certificate No. 2908, granted Oct. 18, 2005). The inflorescence is positioned above the level of the foliage. The flower spike is soft to the touch. Peduncle color is yellow green (approximately RHS 146B-C). Flowering season late spring-summer.

Flowers: The flower buds are 8-10 mm long and 3-4 mm wide. Bud color changes from yellow green (RHS 147B) to violet blue (approximately RHS 90A) prior to opening. Mature flowers have 6 petals with ovate shape. Petal color is violet-blue (approximately RHS 92A-B). Anther filament color is yellow (approximately RHS 11A). Flower diameter range is 9-13 mm. Petal attitude is reflexed.

Fruit: A succulent berry, shape is globose, color of unripe berry is yellow green (RHS 146A) and color of ripe berry is approximately violet blue (RHS 89A), surface texture is smooth and glossy. Seed color is black (RHS 202A).

Environmental tolerances: 'DCMP01' has shown potential for shade tolerance. The winter hardiness of 'DCMP01' is at least to −10 degrees Celsius. 'DCMP01' has been observed to hold color to −6 degrees Celsius.

'DCMP01' has excellent drought tolerance compared with other *Dianella caerulea* varieties, most likely due to its tighter foliage. After severe wilting, 'DCMP01' has been noted to recover with watering.

Disease resistance and susceptibility: 'DCMP01' has excellent tolerance to pests and diseases and good resistance to root rot, which is a common problem in *Dianella caerulea.* Root rot is caused by the disease causing organism *Phytophthora.* Tolerance to pests can refer to no damage from snails, slugs, mites, aphids, whitefly, beetles, caterpillars and moths.

These features and other characteristics of the plant are apparent from the figures.

'DCMP01' Compared to Other Varieties of *Dianella caerulea*

Grouping characteristics used to identify the most similar varieties of common knowledge to 'DCMP01', were short height and dense growth habit. Based on this, 'DBB03' (U.S. Provisional Application Ser. No. 60/614,654, filed Sep. 30, 2004; Australian Plant Breeders Rights Application No. 2003/291, received Oct. 8, 2003) was selected as the most similar suitable comparator for 'DCMP01'. The parent ('Sydney Ecotype') and another form from the Blue Mountains region of New South Wales were also included in the trial. The comparative trial also included 'DCNCO', which has a much taller plant height than 'DCMP01'.

The comparative trial of *Dianella caerulea* 'DCMP01' with other *D. caerulea* including 'DBB03', 'DCNCO', 'Sydney Ecotype', and 'Blue Mountains Ecotype' (unpatented) was carried out in Summer 2002 through Autumn 2003 in Clarendon, New South Wales, Australia. The trial was conducted in open beds. The plants for this trial were propagated from divisions and planted into 130 mm pots filled with soilless potting mix. Nutrition was maintained with slow release fertilizers and pest and disease treatments were applied as required. The plants did not flower during the trial. Trial design included fifteen pots of each variety arranged in a completely randomized design. Measurements were taken from ten plants at random with one sample taken per plant.

In comparing 'DCMP01' with the other *Dianella caerulea* varieties, 'DCMP01' has a more compact habit than 'Sydney Ecotype', 'Blue Mountains Ecotype', 'DBB03' and 'DCNC0'. 'DCMP01' generally has short internodes located on short canes, whereas canes are generally absent on 'DBB03' and 'DCNC0', and the 'Sydney Ecotype' has canes of typical length above the ground. 'DCMP01' has a taller flower spike height compared to 'DCNC0', but a shorter flower spike height compared to 'DBB03'. The 'Sydney Ecotype' has a variable flower spike height. 'DCNC0' has a pale blue colour flower colour, whereas 'DCMP01' has a deeper blue almost purplish flower colour, and the 'Sydney Ecotype' has a variable flower colour. In addition, 'DCMP01' is easier and more productive to propagate from division than other known *Dianella caerulea*. Further comparisons are presented in Table I.

TABLE I

Comparison of *Dianella caerulea* varieties.

| | 'DBB03' | 'DCMP01' | 'DCNCO' | Sydney ecotype | Blue Mountains ecotype |
|---|---|---|---|---|---|
| PLANT: GROWTH HABIT | | | | | |
| | erect | erect | erect | erect to semi-erect | semi-erect to erect |
| PLANT HEIGHT (cm) LSD (P ≦ 0.01) = 6.03 | | | | | |
| mean | 23.4[c] | 24.6[c] | 65.6[a] | 63.0[a] | 49.4[a] |
| std deviation | 2.2 | 2.6 | 5.0 | 5.5 | 8.5 |
| PLANT: DENSITY OF SHOOTS | | | | | |
| | strong | strong | medium-strong | medium | weak |

TABLE I-continued

Comparison of *Dianella caerulea* varieties.

| | 'DBB03' | 'DCMP01' | 'DCNCO' | Sydney ecotype | Blue Mountains ecotype |
|---|---|---|---|---|---|
| STEM: INTERNODE LENGTH | | | | | |
| | short | short | short | long | very long |
| LEAF: WIDTH (mm) LSD (P ≦ 0.01) = 1.97 | | | | | |
| mean | 14.9[c] | 12.2[d] | 13.6[cd] | 17.1[b] | 22.2[a] |
| std deviation | 2.1 | 0.6 | 0.8 | 0.9 | 2.9 |
| LEAF: FOLIAGE COLOUR - overall appearance of leaf | | | | | |
| | blue-green | yellow-green | yellow-green | yellow-green | yellow-green |
| LEAF: COLOUR - waxiness removed | | | | | |
| upper side | 147A | 147A | 147B | 146B | ca 147A |
| lower side | 147A | 147B | 147B | 146B | 147B |
| LEAF: GLAUCOSITY | | | | | |
| | strong | weak | weak | weak | weak |
| LEAF: CROSS SECTION | | | | | |
| | concave | concave | slight concave | slight concave | concave |
| LEAF: PRESENCE OF SPINES ON MARGIN | | | | | |
| | absent | absent | present | present | present |
| LEAF: PROMINENCE OF SPINES ON MARGIN | | | | | |
| | n/a | n/a | medium | medium | very weak |
| LEAF: PRESENCE OF SPINES ON LOWER SIDE MIDRIB | | | | | |
| | absent | absent | present | present | present |
| LEAF: PROMINENCE OF SPINES ON LOWER SIDE MIDRIB | | | | | |
| | n/a | n/a | medium | medium | medium |
| BASAL SHEATH: COLOUR | | | | | |
| | blue-green | red-brown | red-brown | brown to red-brown | red to red-brown |
| BASAL SHEATH: INTENSITY OF ANTHOCYANIN COLOUR | | | | | |
| | absent | weak | medium | medium | strong |

Mean values followed by the same letter are not significantly different at P ≦ 0.01 according to an S-N-K test.

That which is claimed is:

1. A new and distinct variety of *Dianella caerulea* plant named 'DCMP01', substantially as described and illustrated herein.

* * * * *